United States Patent [19]

Strehlke et al.

[11] Patent Number: 5,344,834
[45] Date of Patent: Sep. 6, 1994

[54] FUNCTIONALIZED VINYL AZOLES AND METHODS OF USE

[75] Inventors: Peter Strehlke; Rolf Bohlmann; Martin Schneider; Yukishige Nishino; Hans-Peter Muhn-Seipoldy, all of Berlin, Fed. Rep. of Germany

[73] Assignee: Schering Aktiengesellschaft, Berlin and Bergkamen, Fed. Rep. of Germany

[21] Appl. No.: 802,639

[22] Filed: Dec. 9, 1991

[30] Foreign Application Priority Data

Dec. 7, 1990 [DE] Fed. Rep. of Germany ....... 4039559

[51] Int. Cl.$^5$ .................. A61K 31/41; C07D 233/61; C07D 249/08; C07D 405/06; C07D 409/06; C07D 401/06
[52] U.S. Cl. .................... 514/317; 514/326; 514/383; 514/397; 514/399; 546/208; 546/210; 548/311.1; 548/311.7; 548/314.7; 548/315.1; 548/315.4; 548/336.1; 548/266.4; 548/266.6; 548/267.4; 548/268.8
[58] Field of Search ...................... 548/336, 341, 311.1, 548/311.7, 314.7, 315.4, 336.1, 266.4, 266.6, 267.4, 268.8; 514/397, 399, 317, 326, 383; 546/208, 210

[56] References Cited

U.S. PATENT DOCUMENTS 4,235,620 11/1980 Lewis et al. ..................... 548/101

FOREIGN PATENT DOCUMENTS 0003884 9/1979 European Pat. Off. ............ 548/101
0007010 1/1980 European Pat. Off. .
0227100 7/1987 .
0236940 9/1987 European Pat. Off. ............ 548/101
0299683 1/1989 European Pat. Off. ............ 548/101

Primary Examiner—Floyd D. Higel
Attorney, Agent, or Firm—Millen, White, Zelano & Branigan

[57] ABSTRACT

Pharmaceutical preparations comprising functionalized vinyl azoles of formula I

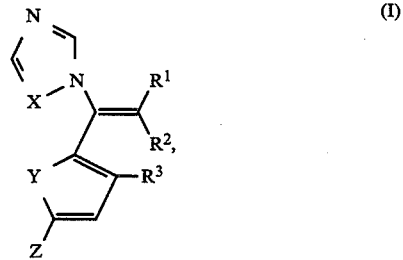

wherein the substituents are as defined herein, including novel compounds, as well as methods of use and methods of their preparation, are provided.

30 Claims, No Drawings

FUNCTIONALIZED VINYL AZOLES AND METHODS OF USE

SUMMARY OF THE INVENTION

This invention relates to functionalized vinyl azoles of formula I

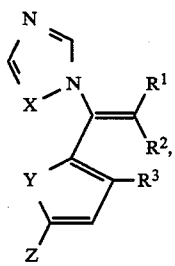

(I)

in which X means an N atom or a CH group, Y means an S atom or a CH=CH group, Z means a cyano group, a fluorine, chlorine or bromine atom and $R^1$ or $R^2$ means optionally esterified carboxyl group,
an optionally substituted carboxylic acid amide group,
an aldehyde group,
an alkylketone or arylketone group,
an optionally substituted sulfonamide group or a nitrile group and the respective other group $R^1$ or $R^2$ independently means a hydrogen atom,
a lower-alkyl group or cycloalkyl group,
an optionally substituted aryl group,
an aralkyl group,
an optionally esterified carboxyl group,
an optionally substituted carboxylic acid amide group,
an aldehyde group,
an alkylketone or arylketone group as well as
a nitrile group or $R^1$ and $R^2$ together with the carbon atom, on which they are bound, mean a 5-, 6- or 7-membered ring, which contains a ketone, ester, lactone, lactam or imide grouping placed so that at least one carbonyl group is conjugated with a vinyl double bond, and $R^3$ means a hydrogen atom or $R^3$ together with $R^2$ means an —O—C=O grouping or an —N—C=O grouping optionally substituted on the N atom whose carbonyl group is conjugated with a vinyl double bond, as well as pharmaceutical preparations containing a pharmaceutically compatible vehicle, use of these vinyl azoles for the production of pharmaceutical agents, vinyl azoles themselves as well as process for their production.

Substituent Z preferably stands for a fluorine atom or a cyano group.

If $R^1$ and/or $R^2$ stands for an esterified carboxyl group (—COOR$^1$ or —COOR$^2$), the latter is esterified first with a straight-chain or branched-chain or cyclic O-alkyl radical with up to 10 carbon atoms, with an O-aryl radical, and aryl is a phenyl or naphthyl radical optionally substituted up to three times by one or more lower-alkyl groups (1–4 carbon atoms) or halogen atoms (F, Cl, Br, I) or an O-aralkyl radical, and in the latter, the aryl and the alkyl fragments have the above-indicated meaning. In this case, the methoxy, ethoxy, propoxy, isopropoxy, isobutoxy, tert-butoxy, cyclohexyloxy, cyclopentyloxy, phenyloxy or 2,6-dichlorophenoxy radical is especially preferred.

If $R^1$ and/or $R^2$ is a substituted carboxylic acid amide group (—CONH$_2$), the carboxyl groups are as defined above, and are substituted with one or two, in the latter case same or different, radicals. These radicals can be straight-chain or branched-chain alkyl radicals with 1 to 10 carbon atoms, or aryl radicals with 6 to 10 carbon atoms optionally substituted up to three times by alkyl groups or halogen atoms as defined above. Further, the amidic nitrogen atom can also be part of a 5- to 8-membered heterocyclic ring, optionally containing one additional ring heteroatom N, O or S; if there is and additional N atom in the ring, it can be substituted by $R^6$, wherein $R^6$ is a hydrogen atom or a straight-chain or branched-chain alkyl group with 1 to 6 carbon atoms.

Quite especially to be emphasized is the substitution of the carboxylic acid amide group with a methyl, ethyl, propyl, phenyl, benzyl radical, two methyl, ethyl, propyl radicals, a phenyl and a methyl, a phenyl and an ethyl, and a benzyl and a methyl radical or a pyrrolidine, piperidine, piperazine, N-methylpiperazine, morpholine or thiomorpholine ring formed together with the amidic nitrogen atom.

The preferred substituents suitable for the substituted sulfonamide group are identical with the preferred N-substituents for the carboxylic acid amide group. First of all, $R^9$ and $R^{10}$ each mean an alkyl substituent with 1 to 10 carbon atoms.

As alkylketone group $R^1$ and/or $R^2$, radical —CO—$R^7$ is preferred, and $R^7$ means a straight-chain or branched-chain alkyl radical with 1 to 10 carbon atoms or a cycloalkyl radical with 3 to 12 carbon atoms, and as an arylketone group, radical -CO-$R^8$ is preferred, and $R^8$ means a phenyl, naphthyl or heteroaryl radical, each optionally substituted up to three times by one or more alkyl, halogen, hydroxy or alkoxy radicals, such as, e.g., a thiophene, furan, pyridine, thiazole, oxazole or diazine ring.

In particular, $R^7$ is a methyl, ethyl, propyl, isopropyl, butyl, isobutyl, pentyl, isopentyl, neopentyl, cyclopentyl or cyclohexyl radical and $R^8$ is a phenyl, hydroxyphenyl, methoxyphenyl or chlorophenyl radical.

If $R^1$ and $R^2$ together with the carbon atom, on which they are bound, form a cyclic system, which should contain at least one carbonyl group, the following ring systems are to be emphasized:

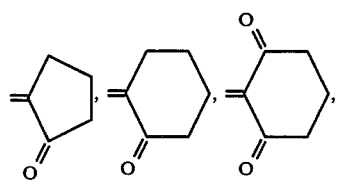

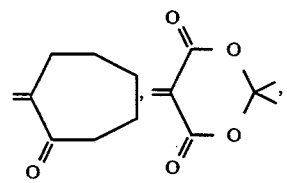

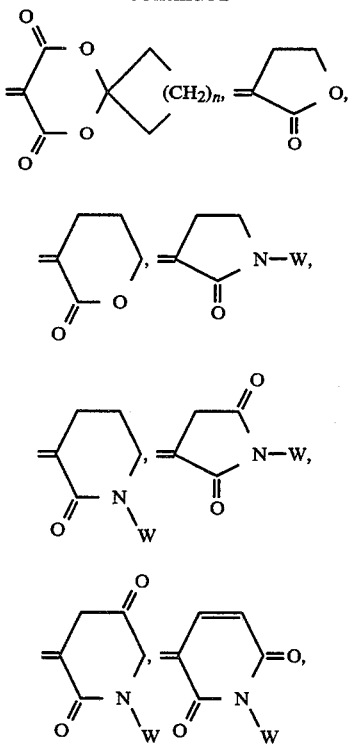

wherein n=2 or 3 and W means a hydrogen atom or an alkyl group with 1–10 C atoms.

With the bridge formed from $R^2$ and $R^3$, the following partial structures result together with the aromatic ring containing Y:

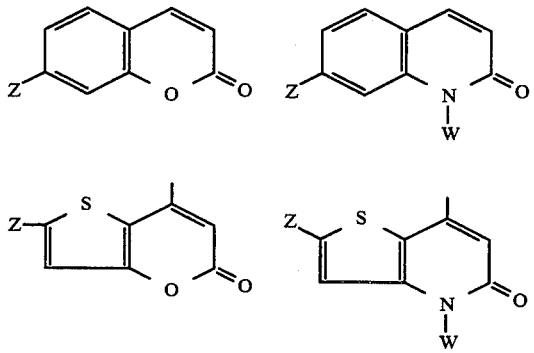

If $R^1$ and $R^2$ in formula I are different, Z- and E-isomeric compounds are produced (except in the case of the cyclical structures above). The invention therefore also comprises the pure Z- or E-compounds as well as any mixtures of both.

The separation of the isomers takes place with standard methods, such as crystallization or chromatography.

The following compounds are preferred:
3-(4-cyanophenyl)-3-(1-imidazolyl)-acrylic acid methyl ester,
3-(4-cyanophenyl)-3-(1-imidazolyl)-acrylic acidtert-butyl ester,
E-3-(4-cyanophenyl)-3-(1-imidazolyl)-acrylic acid,
E-3- (4 -cyanophenyl) -3- (1-imidazolyl) -acrylic acid piperidide,
E-3 - ( 4 -cyanophenyl ) -3- ( 1-imidazolyl ) -acrylic acid methylamide,
3-(4-cyanophenyl)-3-(1-imidazolyl)-acrylonitrile,
4-[1-(1-imidazolyl)-3-oxo-1-butenyl]-benzonitrile,
3-[(4-cyanophenyl)-(1-imidazolyl)-methylene]dihydro-2(3H)-furanone,
3-(5-cyano-2-thienyl)-3-(1-imidazolyl)-acrylic acid-tert-butyl ester,
3-(5-cyano-2-thienyl)-3-(1-imidazolyl)-acrylonitrile,
3-(4-cyanophenyl)-3-(1,2,4-triazol-1-yl)-acrylic acid-tert-butyl ester,
3-(4-cyanophenyl)-3-(1,2,4-triazol-1-yl)-acrylonitrile,
7-cyano-4-(1-imidazolyl)-coumarin,
3-(4-fluorophenyl)-3-(1-imidazolyl)-acrylic acidtert-butyl ester,
3-(4-chlorophenyl)-3-(1-imidazolyl)-acrylic acidtert-butyl ester,
3-(4-bromophenyl)-3-(1-imidazolyl)-acrylic acidtert-butyl ester, and
3-(4-fluorophenyl)-3-(1,2,4-triazol-1-yl)-acrylic acid-tert-butyl ester.

The compounds of formula I are inhibitors of estrogen biosynthesis (aromatase inhibitors). Thus, they are suitable for the treatment of diseases which are caused by estrogens or are dependent on estrogens. Thus, they are suitable for the treatment of estrogen-induced or estrogen-stimulated tumors, such as, for example, breast cancer, endometrial carcinoma, melanoma or prostatic hyperplasia (The Lancet, 1984, 1237–1239).

Said compounds are also valuable for influencing fertility. Thus, male infertility which results from increased estrogen levels can be overcome with the new active ingredients. Further, the compounds can be used in females of child-bearing age as a means of birth control, to inhibit ovulation by removal of estrogen. Aromatase inhibitors are also suitable for preventing impending myocardial infarction, since increased estrogen levels in the male can precede a myocardial infarction (U.S. Pat. No. 4,289,762).

This invention therefore also relates to the use of compounds of formula I for the production of pharmaceutical agents for treating estrogen-induced and estrogendependent diseases.

Phenylalkenones of general formula $R^8C(O)CH=CR^bR^c$, in which $R^a$ means an optionally substituted alkyl or cycloalkyl radical, $R^b$ means a 1,2,4-triazolyl or 1-imidazolyl radical and $R^c$ means a phenyl or naphthyl ring, which optionally can be substituted, among others, with a fluorine, chlorine or bromine atom or a cyano group, are disclosed in EP-A-0 003 884. These phenylalkenones are described as compounds having herbicidal activity. Other herbicidal 1,2,4-triazolylvinyl and imidazolyl vinyl compounds, which, in geminal position in the heterocycle, have a phenyl ring chlorosubstituted in p-position, are disclosed in DE-A-27 38 640.

DE-A 28 26 760 discloses 3-(4-chlorophenyl)-3-(1,2,4-triazolyl)-acrylic acid alkyl esters for use as fungicides and plant-growth regulators.

The above-named compounds, whose medicinal applicability was previously unknown, are encompassed by formula I. On the other hand, the compounds of formula Ia

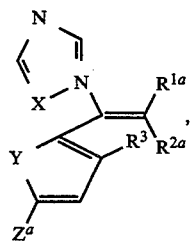

(Ia)

in which

X means an N atom or a CH group,

Y means an S atom or a CH=CH group, $Z^a$ means a cyano group or a fluorine or bromine atom and $R^{1a}$ or $R^{2a}$ means
an optionally esterified carboxyl group,
an optionally substituted carboxylic acid amide group,
an aldehyde group,
an arylketone group,
an optionally substituted sulfonamide group or a nitrile group and the respective other group $R^{1a}$ or $R^{2a}$ means
a hydrogen atom,
a lower-alkyl group or cycloalkyl group,
an optionally substituted aryl group,
an aralkyl group,
an optionally esterified carboxyl group,
an optionally substituted carboxylic acid amide group,
an aldehyde group,
an alkylketone group as well as
a nitrile group or $R^{1a}$ and $R^{2a}$ together with the carbon atom, on which they are bound, mean a 5-, 6- or 7-membered ring, which contains a ketone, ester, lactone, lactam or imide grouping placed so that at least one carbonyl group is conjugated with a vinyl double bond, and $R^3$ means a hydrogen atom or $R^3$ together with $R^{2a}$ means an —O—C=O grouping or an —N—C=O grouping optionally substituted on an N atom whose carbonyl group is conjugated with a vinyl double bond, are new.

The compounds of formula Ia therefore also are an object of this invention.

The radicals possibly or preferably standing for substituents $R^{1a}$, $R^{2a}$ and $R^3$ in the compounds of formula Ia are the same as those of formula I mentioned as possibly or preferably standing for substituents $R^1$, $R^2$ and $R^3$, with the difference that in the compounds of formula Ia, $Z^a$ is not chlorine and $R^{1a}$ and $R^{2a}$ are not an alkylketone group.

Known substances exhibiting an aromatase-inhibiting effect are in addition to steroids also nonsteroidal substances, for example, the various nitrogen heterocycles described in European patent applications EP-A 0165777 to 0165784, the substituted glutaric acid imides described in J. Med. Chem. 1986, 29, pages 1362-1369, the substituted imidazobenzenes described in European patent application EP 0165904, the substituted heterocyclicallysubstituted toluenenitriles described in European patent application EP-A 0236940 and the imidazo- and 5,6,7,8tetrahydro-imidazo[1,5a]pyridines having an optionally substituted phenyl ring, seen from U.S. Pat. No. 4,728,465, from which in particular 5-(p-cyanophenyl)5,6,7,8-tetrahydroimidazo-[1,5a]pyridine, hydrochloride stands out as a greatly effective aromatase inhibitor (Cancer Res. 48, pp. 834–838, 1988).

The compounds of formula I are distinguished relative to the previously known compounds in that they inhibit the enzyme system of the aromatase more strongly and at the same time more selectively. The selective activity is shown in that other enzyme systems are affected to a smaller extent.

The concentrations in which the aromatase activity is inhibited in vitro by the compounds of formula I are in the range of $10^{-7}$ to $10^{-10}$ mol/l.

In comparison with the compounds of EP-A 0236940 that are structurally related, by the introduction of the double bond the compounds of formula I no longer have a chirality center on the carbon atom, on which both the cyanoaryl and the N-heteroaryl radical are present. An enantioselective synthesis or a difficult separation of enantiomers is avoided by the elimination of the chirality center.

The amount of the compounds to be administered varies within a wide range and encompasses all effective amounts. As a function of the condition to be treated and the route of administration, the amount of the administered compounds is 0.0001-10 mg/kg of body weight, preferably 0.001-1 mg/kg of body weight daily. They can be administered analogously to the known aromatase inhibitors discussed above.

For oral administration, capsules, pills, tablets, coated tablets, etc. are suitable. In addition to the active ingredient, the dosage units can contain a pharmaceutically compatible vehicle, such as, for example, starch, sugar, sorbitol, gelatin, lubricants, silicic acids, talc, etc. The individual dosage units for oral administration can contain, for example, 0.05-50 mg of the active ingredient (aromatase inhibitor). The compounds are customarily administered in amounts of from 0.1 to 4.0 g per patient per day.

For parenteral administration, the active ingredients can be dissolved or suspended in a physiologically compatible diluent. As a diluent, very often oils are used with or without adding a solubilizer, a surfactant, a suspension mixture or an emulsifying mixture. As examples for oils used, there can be mentioned: olive oil, peanut oil, cottonseed oil, soybean oil, castor oil and sesame oil.

The compounds can also be used in the form of a depot injection or an implantation preparation, which can be formulated so that a delayed release of active ingredient is made possible.

Implantations can contain as inert materials, for example, biodegradable polymers or synthetic silicones, such as, for example, silicone rubber. The active ingredients can further be worked into, for example, plasters for percutaneous administration.

The compounds of this invention can also be administered in other pharmaceutically customary forms of application, including topically, for example, in solutions, powders, creams, sprays and ointments. These compositions can be formulated conventionally, e.g., as described in U.S. Pat. No. 4,006,243, Examples 81 and. 82, and having a concentration of active agent of, e.g., between 0.5 and 5% by weight.

Without wishing to be bound by theory, the tumorinhibiting activity of imidazole derivatives is based on the inhibition of P-450-dependent enzyme systems (cf., e.g., J. P. Van Wanne and P. A. J. Janssen; J. Med. Chem. 32 (1989) 2231). Also, the action of antifungal therapeutic agents of the series of imidazole-triazole derivatives is based on a blocking of P-450-dependent biochemical reactions (loc. cit.). Further, it is known from the patent literature that azole derivatives have both antifungal and tumor-inhibiting action at the same time (in this connection, cf. EPA 0165777, Eli Lilly). The compounds according to the invention therefore also have antifungal activity against human-, animal- and plant-pathogenic organisms.

The invention further relates to processes for the production of compounds of formula Ia as well as a process for the production of certain compounds of formula I, identified below as compounds of formula I'.

For the production of the compounds of formula Ia, either a) a compound of formula II

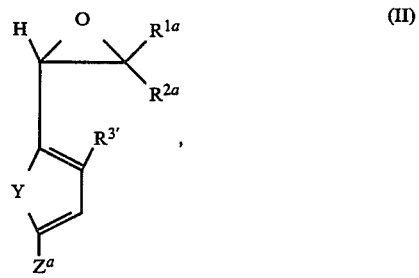

in which $R^{1a}$, $R^{2a}$, Y and $Z^a$ have the meaning indicated in formula Ia and $R^{3'}$ means a hydrogen atom or $R^{3'}$ together with $R^{2a}$ forms a ring of the above-indicated partial structures, reacts with a compound of formula VII

in which

X means an N atom or a CH group and

A means a hydrogen atom, an alkali metal or a trialkylsilyl radical with the same or different straightchain or branched $C_1$–$C_8$ alkyl groups, in an inert solvent at a temperature between room temperature and boiling temperature of the solvent or without solvent, optionally by adding a catalyst first to a compound of formula IIi

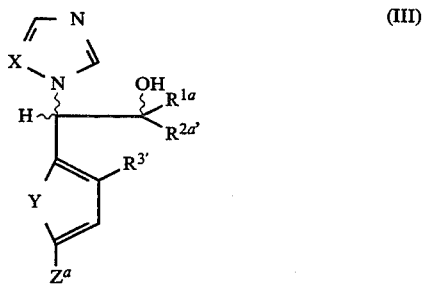

in which $R^{1a}$, $R^{2a}$, $R^{3'}$, X, Y and $Z^a$ have the meaning already indicated in formula II or VII, and the latter is allowed to further react by dehydration above 60° C., optionally in a solvent and optionally by using a catalyst, to a compound of formula Ia, or ii) a compound of formula III

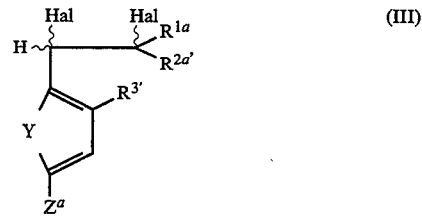

in which $R^1$, $R^2$ and Y have the meaning indicated in formula 1, $R^{3'}$ means a hydrogen atom or together with $R^2$, forms a ring of the above-indicated partial structures, and Hal means halogen atoms, in particular one bromine atom each, reacts with a compound of formula VII according to conventional processes with or without adding a foreign base to a compound of formula I or iii) to an acetylene compound of formula V

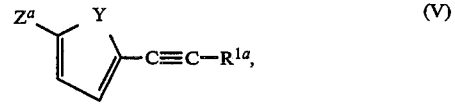

in which Y and $Z^a$ have the meaning indicated in formula I and $R^{1a}$ means an esterified carboxyl group, an optionally substituted carboxylic acid amide group, an aldehyde group, an arylketone group, an optionally substituted sulfonamide group or a nitrile group, and the optionally possible substituents and the alkoxy radicals of the esterified carboxyl group correspond to the definitions already indicated in more detail, is added a compound of formula VII in a solvent between room temperature and boiling temperature of this solvent with forming a compound of formula Iiii

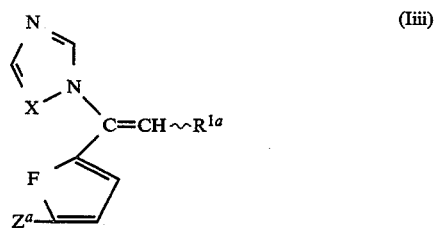

The production of the compounds of formula I according to the invention takes place according to variant i) starting from an epoxide of formula II and an azole of formula VII in a way known in the art.

The addition of the azole is performed in an inert solvent, such as, for example, benzene, toluene, xylene, tetrahydrofuran, dioxane, acetonitrile or dimethylformamide, preferably at a temperature between 60° C. and the boiling temperature of the solvent or without solvent, preferably between 60° C. and 150° C. If necessary, a catalyst, e.g., a metal salt, such as lithium, magnesium, sodium perchlorate, zinc chloride or calcium chloride, can be added (Tetrahedron Letters 31 (1990) 4661).

The dehydration takes place thermally, preferably at temperatures between 100° C. and 200° C. or the boiling temperature of an optionally used solvent, such as, e.g., toluene, chlorobenzene or xylene. As catalysts, inorganic or organic acids, such as, for example, sulfuric acid or p-toluenesulfonic acid are suitable.

The dehydration can also be performed by using dehydrating agents such as thionyl chloride or phosphorus oxychloride with or without a solvent (e.g., dichloromethane, acetonitrile, tetrahydrofuran) at room temperature to boiling temperature of the solvent, preferably between 20° C. and 50° C.

In the reaction of the dihalide of formula III with an azole of formula VII according to ii), methods familiar to one skilled in the art are also involved. The additional use of a foreign base (Heterocycles 15 (1981), 961) can be useful in facilitating the reaction.

First, the exchange of the halogen atom on the benzylic carbon atom takes place and then the elimination of the hydrogen halide. The intermediately-formed monohalogen compound is not isolated.

The necessary initial compounds of formula II or formula III are prepared from the corresponding olefins in a way known in the art by epoxidation or halogenation, preferably bromation: the olefins in turn can be produced conventionally, for example, by Wittig or Knoevenagel reaction of the corresponding feedstocks.

In the addition of an azole of formula VII to an acetylene compound of formula V to be performed in a way known in the art according to variant iii), compounds of formula Iiii are obtained with $R^{2'}=H$ as a Z-/E-isomeric mixture. The production of compounds of formula V is known (e.g., Chem. Ber. 94 (1961) 3005; J. Org. Chem. 30 (1965) 1915). The reaction of compounds of formula V with the optionally substituted azoles VII takes place preferably in solvents such as hydrocarbons (benzene, toluene), ethers (ethyl ether, dioxane, tetrahydrofuran), alcohols (tert-butanol) or halogenated hydrocarbons (dichloromethane, chloroform, 1,2-dichloroethane) between room temperature and boiling temperature of the solvent.

Compounds of formula I'

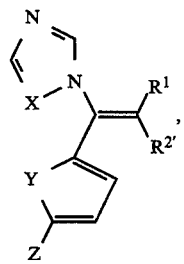

(I')

in which $R^1$, X, Y and Z have the meaning indicated in formula I, $R^{2'}$ means a hydrogen atom or $R^1$ and $R^2$ together with the methylene carbon atom mean a 5-, 6- or 7-membered ring, which contains a ketone, ester, lactone, lactam or imide grouping placed so that at least one carbonyl group is conjugated with a vinyl double bond, are produced, by a compound of formula IV

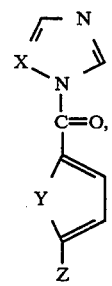

(IV)

in which X, Y and Z have the meaning indicated in formula I, being reacted with a phosphorane of formula VIII

(VIII)

in which

L means a phenyl radical optionally substituted with lower-alkyl($C_{1-6}$), low-alkoxy($C_{1-6}$), or halogen or a straight-chain or branched lower-alkyl radical with 1 to 6 carbon atoms and $R^1$ and $R^{2'}$ have the above-indicated meaning, in an inert solvent between room temperature and boiling temperature of the solvent used.

By reaction of an acylazole of formula IV with a phosphorane of formula VIII, the last-mentioned process variant according to the invention results in the compounds of formula I' (Wittig reaction). As an inert solvent, for example, benzene, toluene, xylene, chlorobenzene, tetrahydrofuran, dioxane, acetonitrile, dimethylformamide or dimethylsulfoxide are used. The reaction temperature is preferably selected above 60° C.

That acylazoles react with a phosphorane in the manner of a Wittig reaction was not previously known. Rather, it is known that acylimidazoles (generally also acylazoles) are good acylation agents (Comprehensive Heterocyclic Chemistry (Eds. A. R. Katritzky, K. T. Potts) Pergamon Press 1984, Volume 4A, page 451 ff). Accordingly, it was to be expected that a Wittig reagent (phosphorane) is acylated on the carbanion, as it is observed, e.g., in the reaction with acid chlorides:

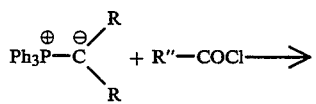

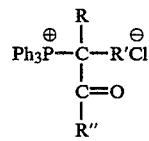

For aliphatic acyl imidazolids, acylation of triphenyl methylene phosphorane is described in M. Miyano et al., J. Org. Chem. 40, 2840 (1975).

It was therefore unexpected and surprising that aromatic acylimidazoles or acylazoles enter into a normal Wittig reaction:

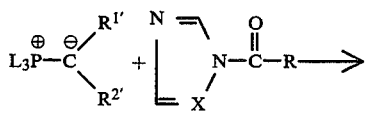

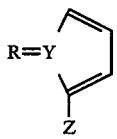

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P 40 39 559.6, filed Dec. 7, 1990, are hereby incorporated by reference.

EXAMPLES

EXAMPLE 1

3-(4-Cyanophenyl)-3-(1-imidazolyl)-acrylic acid methyl ester 2.85 g of 4-cyanobenzoyl chloride, dissolved in 20 ml of ether, is instilled in a solution of 2.4 g of imidazole in 25 ml of tetrahydrofuran and 50 ml of ether. After 10 minutes at room temperature, it is filtered with exclusion of air and the filtrate is concentrated by evaporation in a vacuum. The residue is dissolved in 20 ml of tetrahydrofuran and refluxed with 5.7 g of methoxycarbonylmethylene-triphenylphosphorane for 5 hours. It is added to water extracted with ethyl acetate and the ethyl acetate phase is washed with water. Then, the ethyl acetate phase is extracted three times with 2M hydrochloric acid. The hydrochloric acid phase is alkalized with potassium carbonate and extracted with ethyl acetate. After drying the ethyl acetate phase with sodium sulfate and concentration by evaporation, an oil remains, which thoroughly crystallizes. After suctioning off the crystals with ether, 3.5 g (81%) of a Z-/E-mixture of the title compound is obtained. By recrystallization of ethanol, the E-compound is obtained pure. Mp: 144°–147° C.

EXAMPLE 2

3-(4-Cyanophenyl)-3-(1-imidazolyl)-acrylic acid-tert-butyl ester

Analogously to example 1, with use of tert-butoxycarbonylmethylenetriphenylphosphorane. Yield 37%. After chromatography on silica gel (eluant ethyl acetate) and crystallization from ether, the E-isomer melts at 151°–153° C.

EXAMPLE 3

E-3-(4-Cyanophenyl)-3-(1-imidazolyl)-acrylic acid 100 mg of the E-compound of example 1 is dissolved in 1.5 ml of 10% methanolic potassium hydroxide and left for 15 minutes at room temperature.

Then, it is concentrated by evaporation in a vacuum at 30° C. and the residue is dissolved in 2 ml of water. By adding 1M hydrochloric acid and later 10% acetic acid, it is adjusted to a pH of 5 and extracted with ethyl acetate. After concentration by evaporation of the solvent, 38 mg of the title compound is obtained.

Mp: 230°–246° C.

The hydrochloride of the title compound is obtained as follows:

200 mg of the E-tert-butyl ester of example 2 is stirred with 20 ml of 6 M hydrochloric acid for 2 hours at room temperature. It is concentrated by evaporation in a vacuum, distilled twice more each with toluene and methylene chloride and 195 mg (100%) of E-3-(4-cyanophenyl)-3-(1-imidazolyl)-acrylic acid, hydrochloride, is obtained.

EXAMPLE 4

E-3-(4-Cyanophenyl)-3-(1-imidazolyl)-acrylic acid piperidide 190 mg of the hydrochloride of example 3, 196 mg of 2-chloro-1-methylpyridinium iodide, 57 mg of piperidine, 290 mg of tributylamine and 12 ml of methylene chloride are refluxed for 20 hours. The acid phase is separated and saturated with potassium carbonate. It is extracted with ethyl acetate, the ethyl acetate phase is concentrated by evaporation and the low-boiling material is distilled off from the residue at 100° C. and 0.01 mbar. The residue is chromatographed on silica gel. With methylene chloride/isopropanol (0.5–4% isopropanol), 52 mg of crystalline product is obtained with a melting point of 160°–165° C.

EXAMPLE 5

E-3-(4-Cyanophenyl)-3-(1-imidazolyl)-acrylic acid methylamide 1.35 g of methylammonium chloride in 10 ml of toluene is mixed under argon with 7.5 ml of trimethylaluminum in 10 ml of toluene by instillation and stirred for 2 hours at room temperature. 50 mg of the E-methyl ester of example 1 is mixed in 2 ml of toluene with 2 ml of the above-produced reagent. It is stirred for 6 hours at 80° C., then mixed at room temperature with 1M hydrochloric acid and extracted with ether. The acid phase is alkalized with potassium carbonate and extracted with ethyl acetate. After washing with water and drying, the ethyl acetate phase is concentrated by evaporation. 30 mg of the title compound (50%) remains; melting range: 172°–180° C.

EXAMPLE 6

3-(4-Cyanophenyl)-3-(1-imidazolyl)-acrylonitrile

Analogously to example 1, the title compound is obtained with use of cyanomethylenetriphenylphosphorane. The E-isomer is obtained pure from ethanol; mp: 188°–193° C.

EXAMPLE 7

4-[1-(1-Imidazolyl)-3-oxo-1-butenyl]-benzonitrile a) Analogously to example 1, with use of acetonylidine-triphenylphosphorane. A Z-/E-mixture of the title compound is obtained.

b) By stirring 3.02 g of 4-cyanobenzaldehyde and 7.32 g of acetonylidene-triphenylphosphorane in 50 ml of dichloromethane and then recrystallizing from isopropanol, 3.15 g (80%) of 4-(3-oxobutenyl)-benzonitrile is obtained. 1.71 g of it is mixed in 20 ml of dichloromethane with 20 ml of a 0.5 M solution of bromine in dichloromethane. After decolorization, the solvent is drawn off in a vacuum. The remaining oil is refluxed with 0.95 g of imidazole and 7 ml of triethylamine in 40 ml of toluene for 2 hours. A precipitate is filtered off, the filtrate is distributed in ethyl acetate-2M hydrochloric acid, the hydrochloric acid phase is alkalized with potassium carbonate and extracted with ethyl acetate. 1.2 g of a crude product is obtained, which, after recrystallization from isopropanol, yields the Z-isomer with mp. 131°–135° C. After chromatography of the mother liquor on silica gel (eluant ethyl acetate), the E-isomer is obtained from ethyl acetate/ether as crystals of mp: 123°–126° C.

EXAMPLE 8

3-[(4-Cyanophenyl)-(1-imidazolyl)-methylene)-dihydro-2(3H)-furanone

Analogously to example 1, with use of 3-(triphenylphosphoranylidine)-dihydro-2(3H)-furanone in the solvent toluene under reflux (20 hours). Chromatography of the crude product on silica gel (eluant dichloromethane/ methanol 99:1) and recrystallization from isopropanol produces the title compound in E-form with mp: 194°–197° C.

EXAMPLE 9

3-(5-Cyano-2-thienyl)-3-(1-imidazolyl)-acrylic acid tert-butyl ester

The acid chloride is produced from 2 g of 5-cyanophiophene-2-carboxylic acid by boiling with thionyl chloride and distilling off excess thionyl chloride. The acid chloride is dissolved in 10 ml of ether and mixed with 1.9 ml of N-trimethylsilylimidazole. It is concentrated by evaporation in a vacuum, dissolved in a mixture of 150 ml of tetrahydrofuran and 50 ml of acetonitrile and mixed with 4.9 g of tert-butoxycarbonylmethylenetriphenylphosphorane. It is refluxed for 20 hours and worked up as in example 1. The crude product is chromatographed on silica gel using dichloromethane with 1-2% isopropanol. 2.4 g (63%) of the title compound is obtained as a Z-/E-mixture. The E-isomer is obtained pure by recrystallization from isopropanol; mp: 90°–91° C.

EXAMPLE 10

3-(5-Cyano-2-thienyl)-3-(1-imidazolyl)-acrylonitrile

Analogously to example 9, with use of cyanomethylenetriphenylphosphorane, a Z-/E-mixture of the title compound is obtained. The E-isomer is obtained pure from ethanol; mp: 129°–133° C.

EXAMPLE 11

3-(4-Cyanophenyl)-3-(1,2,4-triazol-1-yl)-acrylic acid-tert-butyl ester

Analogously to example 9, with use of 1-trimethylsilyl-1,2,4-triazole and tert-butoxycarbonylmethylenetriphenylphosphorane Z-isomer: mp: 132°–133° C.
E-isomer: mp: 83°–85° C.

EXAMPLE 12

3-(4-Cyanophenyl)-3-(1,2,4-triazol-1-yl)-acrylonitrile

Analogously to example 9, with use of 1-trimethylsilyl-1,2,4-triazole and cyanomethylene-triphenylphosphorane.

EXAMPLE 13

7-Cyano-4-(1-imidazolyl)-coumarin 5 g of 7-hydroxycoumarin in 25 ml of pyridine is mixed by instillation under argon at 0° C. with a mixture of 8.1 ml of trifluoromethanesulfonic acid anhydride and 65 ml of pyridine. It is stirred for 20 more hours at room temperature, poured on 400 ml of ice-cold, semiconcentrated hydrochloric acid and extracted with ethyl acetate. After washing the ethyl acetate phase with semiconcentrated hydrochloric acid, water and potassium bicarbonate solution in succession, it is dried and concentrated by evaporation. 6.9 g of 7-hydroxycoumarintrifluoromethanesulfonic acid ester is obtained; mp: 75°–76° C.

3 g of it is refluxed with 960 mg of potassium cyanide, 2.4 g of tetrakis-(triphenylphosphine)-palladium(O) and 30 mg of 1,4,7,10,13,16-hexaoxacyclooctadecane (18—crown-6) in 180 ml of tetrahydrofuran for 5 hours. It is diluted with water, extracted with ethyl acetate and the ethyl acetate phase is washed in succession with 1M sodium hydroxide solution, water and common salt solution. After concentration by evaporation in a vacuum, it is recrystallized from ethanol and 975 mg of 7-cyanocoumarin is obtained; mp: 217°–225° C.

This material is dissolved in 95 ml of dichloromethane, mixed with 10 ml of bromine and stirred under action of light (100 W) for 4 days. Then, it is concentrated by evaporation in a vacuum. The crystals are suctioned off with ether. 1.2 g of 3,4-dibromo-7-cyano 2-chromanone is obtained; mp: 220°–230° C.

The dibromo compound is refluxed with 372 mg of imidazole and 2.52 ml of triethylamine in 20 ml of toluene for 7 hours. The solution is distributed between 1M hydrochloric acid and ether, the acid water phase is separated and it is alkalized with potassium carbonate. After extraction with ethyl acetate and concentration of the solvent by evaporation, the remaining crystals are suctioned off with ether, dried at 50° C. in a vacuum and 140 mg of the title compound of melting point 260°–268° C. is thus obtained.

EXAMPLE 14

3-(4-Cyanophenyl)-3-(1-imidazolyl)-acrylic acid methyl ester

4-Cyanophenyl-propiolic acid methyl ester is obtained from 10 g of 4-cyanobenzoyl chloride and 40 g of methoxy-carbonylmethylene-triphenylphosphorane (yield 5.5 g; mp: 103°–106° C.) analogously to Chem. Ber. 94 (1961) 3005 and further reacted as follows:

a) 185 mg of the ester and 75 mg of imidazole are refluxed in 5 ml of tetrahydrofuran for 20 hours. It is distributed between 1M hydrochloric acid and ether, the acid water phase is separated, it is alkalized with potassium carbonate and then extracted with ethyl acetate. After drying and concentration by evaporation, 150 mg of crystals, which represent a Z:E mixture in the ratio 5.2:1 of the product produced in example 1, is obtained.

b) 185 mg of the ester, 75 mg of imidazole and 0.07 mg of triethylamine in 5 ml of tetrahydrofuran are reacted and worked up as in a). 150 mg of product is obtained; Z:E =6.5:1.

c) 185 mg of ester and 155 mg of N-trimethylsilylimidazole in 5 ml of tetrahydrofuran are treated as in a). 100 mg of product is obtained; Z:E =4:1.

EXAMPLE 16

3-(4-Fluorophenyl)-S-(1-imidazolyl)-acrylic acidtert-butyl ester

Analogously to example 9, with use of 4-fluorobenzoic acid, a Z-/E-mixture of the title compound is obtained. After chromatography and recrystallization, the E-isomer is obtained pure.

Mp: 90°–93° C.

EXAMPLE 16

3-(4-Chlorophenyl)-3-(1-imidazolyl)-acrylic acidtert-butyl ester

Analogously to example 9, with use of 4-chlorobenzoic acid. The E-isomer melts at 114°–121° C. (from cyclohexane).

EXAMPLE 17

3-(4-Bromophenyl)-3-(1-imidazolyl)-acrylic acidtert-butyl ester

Analogously to example 9, with use of 4-bromobenzoic acid. The E-isomer melts at 131°–132° C. (from isopropanol).

EXAMPLE 18

3-(4-Fluorophenyl)-3-(1,2,4-triazol-1-yl)-acrylic acid-tert-butyl ester

Analogously to example 9, with use of 4-fluorobenzoic acid and 1-trimethylsilyl-1,2,4-triazole. The E-isomer melts at 72°–74° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical preparation comprising an effective amount of a vinyl azole of formula I (I)

wherein
X is N or CH,
Y is S or CH=CH,
Z is cyano, and one of $R^1$ or $R^2$ is carboxyl unsterified or esterified with $C_{1-10}$ straightchain, branched-chain or cyclic O-alkyl; or with O-aryl, wherein aryl is phenyl or naphthyl, unsubstituted or substituted by 1-3 $C_{1-4}$-alkyl or halogen; or with an O-aralkyl, wherein aryl and alkyl have the indicated meanings, carboxylic acid amide, wherein the carboxyl has the above-indicated meaning; unsubstituted or substituted with 1-2 same or different $C_{1-10}$ straight-chain or branched-chain alkyl; or $C_{6-10}$ aryl, unsubstituted or substituted by 1-3 C1-4 alkyl or halogen; and the amide N can also be part of a 5-8 membered heterocyclic ring, containing no additional heteroatom or an additional ring heteroatom N, O or S, and the additional N is unsubstituted or substituted by $R^6$, wherein $R^6$ is H or $C_{1-6}$ straight-chain or branched-chain alkyl, aldehyde, alkylketone —CO—$R^7$, wherein $R^7$ is a straight-chain or branched-chain $C_{1-10}$ alkyl or $C_{3-12}$ cycloalkyl, arylketone —CO—$R^8$, wherein $R^8$ is phenyl, naphthyl or heteroaryl, unsubstituted or substituted 1-3 times by $C_{1-4}$ alkyl, halogen, hydroxy or $C_{1-4}$ alkoxy, sulfonamide, unsubstituted or substituted by $R^6$, or cyano;
and the respective other $R^1$ or $R^2$ is hydrogen, $C_{1-4}$ lower-alkyl or cycloalkyl, unsubstituted or substituted aryl, aralkyl, unesterified or esterified carboxyl, unsubstituted or substituted carboxylic acid amide, aldehyde, alkylketone or arylketone or cyano, each as defined above;
$R^1$ and $R^2$ together with the carbon atom on which they are bound form a 5-, 6- or 7-membered ring, which further contains a ketone, ester, lactone, lactam or imide, wherein at least one carbonyl is conjugated with a vinyl double bond; and
$R^3$ is hydrogen; or
$R^3$ together with $R^2$ are
—O—C=O or —N—C=O, unsubstituted or substituted on the N,
wherein
the carbonyl is conjugated with a vinyl double bond, and a pharmaceutically acceptable excipient, wherein the preparation is in a unit dosage form for oral administration, is sterile for parenteral administration, or is a cream or ointment for topical administration.

2. A pharmaceutical preparation according to claim 1, wherein $R^1$ or $R^2$ is hydrogen.

3. A pharmaceutical preparation according to claim 1, wherein $R^1$ and $R^2$ together with the carbon on which they are bound form a 5-, 6- or 7-membered ring and $R^3$ is hydrogen.

4. A pharmaceutical preparation according to claim 1, wherein $R^3$ is hydrogen.

5. A pharmaceutical preparation according to claim 1, wherein $R^3$ together with $R^2$ are —O—C=O or —N—C=O .

6. A pharmaceutical preparation according to claim 1, wherein $R^1$ and/or $R^2$ are carboxyl esterified with a straight-chain or branchedchain or cyclic $C_{1-10}$O-alkyl, with O-aryl, and aryl is phenyl or naphthyl, unsubstituted or substituted one or more times by $C_{1-4}$ lower-alkyl, F, Cl, Br, I, or by O-aralkyl, wherein aryl and alkyl are as defined above.

7. A pharmaceutical preparation according to claim 1, wherein $R^1$ and/or $R^2$ are carboxylic acid amide substituted one or two times by same or different straight-chain or branched-chain $C_{1-10}$-alkyl, $C_{6-10}$-aryl radicals, unsubstituted or substituted up to three times by alkyl or halogen, or wherein both alkyls on the amidic nitrogen together with the amidic nitrogen form a 5- to 8-membered heterocyclic ring, containing no additional heteroatoms or an additional ring heteroatom N, O or S, and, if there is an additional N in the ring, it is unsubstituted or substituted by $R^6$, wherein $R^6$ is H or straight-chain or branched-chain $C^6$-alkyl.

8. A pharmaceutical preparation according to claim 1, wherein $R^1$ and/or $R^2$ is alkylketone —CO—$R^7$, and $R^7$ is straight-chain or branched-chain $C_{1-10}$ alkyl or $C_{3-12}$-cycloalkyl.

9. A pharmaceutical preparation according to claim 1, wherein $R^1$ and/or $R^2$ is arylketone —CO—$R^8$, and $R^8$ is phenyl, naphthyl or heteroaryl unsubstituted or substituted by alkyl, halogen, hydroxy or alkoxy.

10. A pharmaceutical preparation according to claim 1, wherein $R^1$ or $R^2$ is sulfonamide —$SO_2NR^9R^{10}$, and $R^9$ and $R^{10}$ are each, independently, a straight-chain or branched-chain $C_{1-10}$-alkyl, $C_{8-10}$-aryl, unsubstituted or substituted one to three times by alkyl or halogen, or wherein both alkyls on the amidic nitrogen together with the amidic nitrogen form a 5- to 8-membered heterocyclic ring, containing no additional heteroatoms or an additional ring heteroatom N, O or S, and, if there is an additional N in the ring, it is unsubstituted or substituted by $R^6$, wherein $R^6$ is H or straight-chain or branched-chain $C_{1-6}$-alkyl.

11. A pharmaceutical preparation according to claim 6, wherein the carboxyl is esterified with methoxy, ethoxy, propoxy, isopropoxy, isobutoxy, tert-butoxy, cyclohexyloxy, cyclopentyloxy, phenyloxy, or 2,6-dichlorophenoxy.

12. A pharmaceutical preparation according to claim 7, wherein the carboxylic acid amide is substituted with methyl, ethyl, propyl, phenyl or benzyl; two methyls, ethyls or propyls; phenyl and methyl; phenyl and ethyl; or benzyl and methyl; or wherein the substituents on the amidic nitrogen together with the amidic nitrogen form a pyrrolidine, piperidine, piperazine, N-methylpiperazine, morpholine or thiomorpholine ring.

13. A pharmaceutical preparation according to claim 8, wherein $R^7$ is methyl, ethyl, propyl, isopropyl, butyl, isobutyl, pentyl, cyclopentyl or cyclohexyl.

14. A pharmaceutical preparation according to claim 9, wherein $R^8$ is phenyl, hydroxyphenyl, methoxyphenyl or chlorophenyl.

15. A pharmaceutical preparation according to claim 10, wherein $R^9$ and $R^{10}$ are methyl, ethyl, propyl, phenyl or benzyl; two methyls, ethyls or propyls; phenyl and methyl; phenyl and ethyl; or benzyl and methyl; or wherein the substituents on the amidic nitrogen together with the amidic nitrogen form a pyrrolidine, piperidine, piperazine, Nmethylpiperazine, morpholine or thiomorpholine ring.

16. A pharmaceutical preparation according to claim 15, wherein $R^9$ and $R^{10}$ is each alkyl.

17. A pharmaceutical preparation according to claim 3, wherein $R^1$ and $R^2$ together with the carbon on which they are bound form a

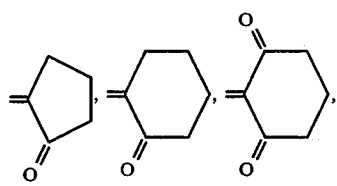

-continued

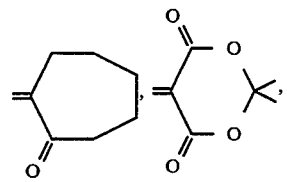

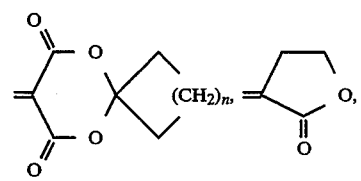

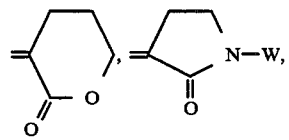

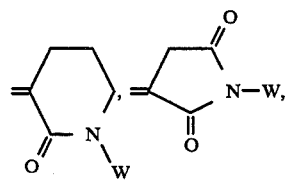

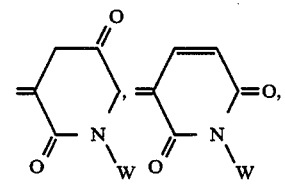

wherein n is 2 or 3 and W is hydrogen or $C_{1-6}$-alkyl.

18. A pharmaceutical preparation according to claim 5, wherein $R^2$ and $R^3$ together with the aromatic ring containing Y form a

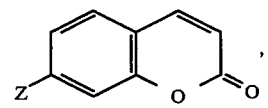

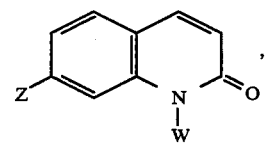

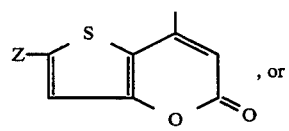

, or

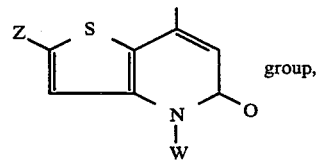

group, wherein W is hydrogen or alkyl.

19. A pharmaceutical preparation according to claim 1, wherein the vinyl azole is 3-(4-cyanophenyl)-3-(1-imidazolyl)-acrylic acid methyl ester, 3-(4-cyanophenyl)-3-(1-imidazolyl)-acrylic acid tert-butyl ester, E-3-(4-cyanophenyl)-3-(1-imidazolyl)-acrylic acid, E-3-(4-cyanophenyl)-3-(1-imidazolyl)-acrylic acid piperidide, E-3-(4-cyanophenyl)-3-(1-imidazolyl)-acrylic acid methylamide, 3-(4-cyanophenyl)-3-(1-imidazolyl)-acrylonitrile, 4-[1-(1-imidazolyl)-3-oxo-1-butenyl]-benzonitrile, 3-[(4-cyanophenyl)-(1-imidazolyl)-methylene]dihydro-2(3H)-furanone, 3-(5-cyano-2-thienyl)-3-(1-imidazolyl)-acrylic acid-tert-butyl ester, 3-(5-cyano-2-thienyl)-3-(1-imidazolyl)acrylonitrile, 3-(4-cyanophenyl)-3-(1,2,4-triazol-1-yl)-acrylic acid-tert-butyl ester, 3-(4-cyanophenyl)-3-(1,2,4-triazol-1-yl)acrylonitrile, or 7-cyano-4-(1-imidazolyl)-coumarin;

20. A pharmaceutical preparation of claim 1, which is sterile.

21. A pharmaceutical preparation of claim 1, wherein, when one of $R^1$ or $R^2$ is arylketone, the other is cycloalkyl, unsubstituted or substituted aryl, aralkyl, unesterified or esterified carboxyl, unsubstituted or substituted carboxylic acid amide, aldehyde, arylketone or cyano.

22. A pharmaceutical preparation of claim 1, wherein the parenteral administration is in the form of a sterile depot injection.

23. A pharmaceutical preparation of claim 1, wherein the parenteral administration is in the form of a sterile implant.

24. A method of inhibiting estrogen biosynthesis comprising administering an effective amount of a pharmaceutical preparation of claim 1.

25. A method of treating estrogen-induced or estrogen-dependent tumors, comprising administering an effective amount of a pharmaceutical preparation of claim 1.

26. A method of treating estrogen-induced male infertility, comprising administering an effective amount of a pharmaceutical preparation of claim 1.

27. A method of inhibiting ovulation, comprising administering an effective amount of a pharmaceutical preparation of claim 1.

28. A vinyl azole of formula 1a

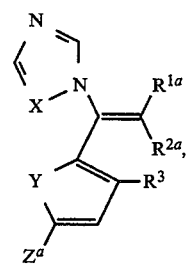

wherein
X is N or CH,
Y is S or CH=CH,
$Z^a$ is cyano and
$R^{1a}$ or $R^{2a}$ is carboxyl unesterified or esterified with C straightchain or branched-chain or cyclic O-alkyl; or with O-aryl, wherein aryl is phenyl or naphthyl, unsubstituted or substituted 1-3 times by $C_{1-4}$-alkyl or halogen; or with O-aralkyl, wherein aryl and alkyl have the indicated meanings, carboxylic acid amide, wherein the carboxyl has the above-indicated meaning unsubstituted or substituted 1-2 times by same or different $C_{1-10}$ straight-chain or branched-chain alkyl; or $C_{6-10}$ aryl unsubstituted or substituted 1-3 times by $C_{1-4}$ alkyl or halogen, and the amide N is optionally can be part of a 5-8 membered heterocyclic ring, containing no additional heteroatom or an additional ring heteroatom N, O or S, and the additional N is unsubstituted or substituted by $R^6$, wherein $R^6$ is H or $C_{1-6}$ straight-chain or branched-chain alkyl, aidehyde, arylketone -CO-$R^8$, wherein $R^a$ is phenyl, naphthyl or heteroaryl, unsubstituted or substituted 1-3 times by $C_{1-4}$ alkyl, halogen, hydroxy or $C_{1-4}$ alkoxy, sulfonamide, unsubstituted or substituted by $R^6$, or cyano and the respective other $R^{TM}$ or $R^{2a}$ is hydrogen, lower-alkyl or cycloalkyl, unsubstituted or substituted aryl, aralkyl, unesterified or esterified carboxyl, unsubstituted or substituted carboxylic acid amide, aldehyde, arylketone or cyano, each as defined above, with the proviso that $R^{TM}$ and $R^{2a}$ are not simultaneously hydrogen and arylketone, $R^{2a}$ and $R^{2a}$ together with the carbon on which they are bound form a 5-, 6- or 7-membered ring, which further contains a ketone, ester, lactone, lactam or imide, wherein at least one carbonyl is conjugated with a vinyl double bond; and $R^3$ [means]is hydrogen; or $R^3$ together with $R^{2a}$ are —OC —O—N—C =or unsubstituted or substituted on the N, wherein the carbonyl group is conjugated with a vinyl double bond.

29. A pharmaceutical preparation comprising an effective amount of a compound of claim 28 and a pharmaceutically acceptable excipient.

30. A vinyl azole of claim 28, wherein, when one of $R^{1a}$ or $R^{2a}$ is arylketone, the other is cycloalkyl, unsubstituted or substituted aryl, aralkyl, unesterified or esterified carboxyl, unsubstituted or substituted carboxylic acid amide, aldehyde, arylketone or cyano.

* * * * *

UNITED STATES PATENT AND TRADEMARK OFFICE
CERTIFICATE OF CORRECTION

PATENT NO. : 5,344,834
DATED : September 6, 1994
INVENTOR(S) : Peter STREHLKE et al.

It is certified that error appears in the above-indentified patent and that said Letters Patent is hereby corrected as shown below:

Claim 17, Column 18, Line 35: Insert -- or -- between the last two subsitute Benzene rings.

Claim 28, Column 20, Line 28: Insert -- - -- between 8 and membered.

Claim 28, Column 20, Line 34: Delete "R$^a$" and insert -- R$^8$ --.

Claim 28, Column 20, Line 38: Delete "R$^{™}$" and insert -- R$^{1a}$ --.

Claim 28, Column 20, Line 44: Delete "R$^{™}$" and insert -- R$^{1a}$ --.

Signed and Sealed this

Sixth Day of December, 1994

Attest:

BRUCE LEHMAN

*Attesting Officer*  *Commissioner of Patents and Trademarks*